United States Patent [19]

Fréchet et al.

[11] Patent Number: 4,585,770
[45] Date of Patent: Apr. 29, 1986

[54] NOVEL 6-AMINO-7-HYDROXY-4,5,6,7-TETRAHYDRO-IMIDAZO[4,5,1-J-K][1]-BENZAZEPIN-2-(1H)-ONE

[75] Inventors: Daniel Fréchet, Paris; Lucien Nédelec, Le Raincy; Guy Plassard, Savigny S/Orge; Neil L. Brown, Paris, all of France

[73] Assignee: Roussel Uclaf, Paris, France

[21] Appl. No.: 541,085

[22] Filed: Oct. 12, 1983

[30] Foreign Application Priority Data

Oct. 12, 1982 [FR] France ................... 82 17054

[51] Int. Cl.⁴ .................. A61K 31/55; A61K 31/645; C07D 487/04
[52] U.S. Cl. .................. 514/214; 260/244.4; 260/245.6; 548/329
[58] Field of Search ........... 260/245.6, 244.4; 424/273 B, 267; 514/214

[56] References Cited

U.S. PATENT DOCUMENTS 2,320,439  6/1943  Kumetat et al. ............ 546/84
3,200,123  8/1965  Richardson et al. ......... 546/84
4,335,135  6/1982  Nédelec et al. ............ 548/436

Primary Examiner—Alton D. Rollins
Attorney, Agent, or Firm—Bierman, Peroff & Muserlian

[57] ABSTRACT

Novel 6-amino-7-hydroxy-4,5,6,7-tetrahydroimidazo[4,5,1-j-k][1]-benzazepin-2-(1H)-one derivatives of the formula

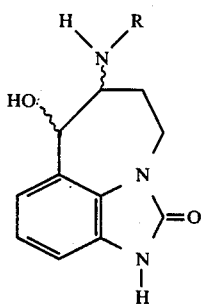

wherein R is selected from the group consisting of hydrogen, alkyl of 1 to 8 carbon atoms optionally substituted with a hydroxyl, aryl and aryloxy of 6 to 10 carbon atoms, cycloalkyl of 3 to 7 carbon atoms optionally interrupted with a heteroatom optionally substituted with alkyl of 1 to 4 carbon atoms and the wavy lines indicates that the 7-OH and 6-amino have the trans configuration and their non-toxic, pharmaceutically acceptable acid addition salts having remarkable antihypertensive and hypotensive activity and vasodilatatory activity and their preparation.

18 Claims, No Drawings

NOVEL 6-AMINO-7-HYDROXY-4,5,6,7-TETRAHYDRO-IMIDAZO[4,5,1-J-K][1]-BENZAZEPIN-2-(1H)-ONE

OBJECTS OF THE INVENTION

It is an object of the invention to provide the novel compounds of formula I and their non-toxic, pharmaceutically acceptable acid addition salts and a process for their preparation.

It is another object of the invention to provide novel antihypertensive and hypotensive compositions and a novel method of treating arterial hypertension in warm-blooded animals.

These and other objects and advantages of the invention will become obvious from the following detailed description.

THE INVENTION

The novel compounds of the invention are selected from the group consisting of 6-amino-7-hydroxy-4,5,6,7-tetrahydro-imidazo[4,5,1-j-k][1]-benzazepin-2-(1H)-one derivatives of the formula I

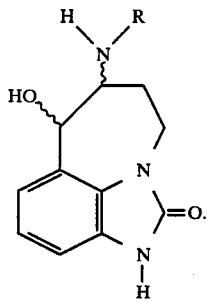

wherein R is selected from the group consisting of hydrogen, alkyl of 1 to 8 carbon atoms optionally substituted with a hydroxyl, aryl and aryloxy of 6 to 10 carbon atoms, cycloalkyl of 3 to 7 carbon atoms optionally interrupted with a heteroatom optionally substituted with alkyl of 1 to 4 carbon atoms and the wavy lines indicates that the 7-OH and 6-amino have the trans configuration and their non-toxic, pharmaceutically acceptable acid addition salts.

Examples of R are hydrogen, alkyl of 1 to 8 carbon atoms optionally containing a hydroxy such as methyl, ethyl, isopropyl, 2,2-dimethylpropyl, n-propyl, n-butyl, n-pentyl, 2-hydroxyethyl and hydroxymethyl; aryl such as phenyl; aryloxy such as phenoxy; cycloalkyl of 3 to 7 carbon atoms such as cyclopropyl, cyclobutyl, cyclopentyl, cyclohexyl and cycloheptyl and the heteroatom is preferably nitrogen which preferably is substituted with methyl.

Examples of suitable acids for the non-toxic, pharmaceutically acceptable acid addition salts are inorganic acids such as hydrochloric acid, hydrobromic acid, nitric acid, sulfuric acid and phosphoric acid and organic acids such as acetic acid, formic acid, propionic acid, benzoic acid, maleic acid, fumaric acid, succinic acid, tartaric acid, citric acid, oxalic acid, glyoxylic acid, aspartic acid, alkanesulfonic acids such as methane sulfonic acid and ethane sulfonic acid, arylsulfonic acids such as benzene sulfonic acid and p-toluene sulfonic acid and arylcarboxylic acids.

Among the preferred compounds of the invention are those of formula I wherein R is hydrogen or alkyl of 1 to 5 carbon atoms and their non-toxic, pharmaceutically acceptable acid addition salts. Specific preferred compounds are (6RS,trans)6-amino-7-hydroxy-4,5,6,7-tetrahydro-imidazo[4,5,1-j-k][1]-benzazepine-2(1H)-one, (6RS,trans) 6-ethylamino-7-hydroxy-4,5,6,7-tetrahydro-imidazo[4,5,1-k][1]-benzazepin-2(1H)-one, (6RS, trans) 6-methylamino-7-hydroxy-4,5,6,7-tetrahydro-imidazo[4,5,1-j-k][1]-benzazepin-2(1H)-one and (6RS,trans) 6-isopropylamino-7-hydroxy-4,5,6,7-tetrahydroimidazo[4,5,1-j-k][1]-benzazepin-2(1H)-one and their non-toxic, pharmaceutically acceptable acid addition salts.

The novel process of the invention for the preparation of the compounds of formula I comprises reacting a compound of the formula

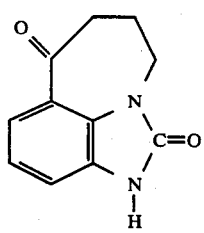

with an alkyl nitrite, preferably in the presence of an acid to form a compound of the formula

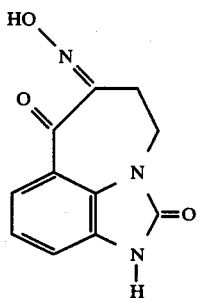

reducing the latter to obtain a compound of the formula

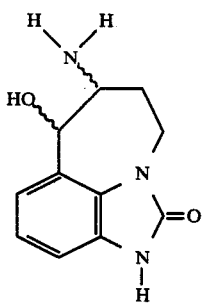

which may be isolated and optionally salified or after protecting any free —NH₂ groups preferably as a benzyl derivative, reacting the latter with an alkylating agent which after deblocking forms a compound of the formula

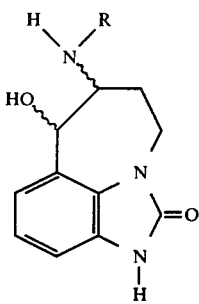  I_B wherein the wavy lines have the above definition and R is other than hydrogen which may be isolated and optionally salified or reacted with a carbonyl derivative of the formula

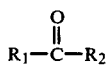  IV wherein R$_1$ and R$_2$ are such that

have the significance of R other than hydrogen and methyl in the presence of a tertiary amine and then with a reducing agent to obtain a compound of the formula

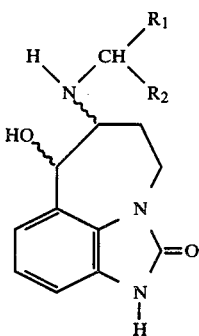  I_C which may be isolated and optionally salified.

In a preferred mode of the process, the reaction with the alkyl nitrite is effected with tert.-butyl nitrite but other nitrites such as isoamyl nitrite may be used and the reaction is effected in the presence of a base but preferably in the presence of an acid such as hydrochloric acid. The reduction of the compounds of formula III is preferably effected with catalytic hydrogenation or with sodium borohydride.

The alkylation of the compound of formula I$_A$ is advantageously effected after blockage, for example, as a N-benzyl derivative of the compound of formula I$_A$ with an alkyl halide such as chloride or iodide but preferably bromide in the presence or absence of an acid binding agent such as an alkali metal carbonate like sodium carbonate or an alkali metal hydroxide like potassium hydroxide or a tertiary amine like triethylamine after which the protective group is removed such as by catalytic hydrogenation in the case of benzyl. The tertiary amine used with the carbonyl derivative of formula IV is preferably triethylamine and the reducing agent is preferably an alkali metal borohydride or cyanoborohydride, especially sodium.

Another facet of the invention is a process for the preparation of compounds of formula II comprising reacting a compound of the formula

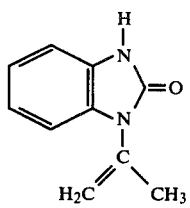  V with an alkyl 4-halobutyrate of the formula

Hal—(CH$_2$)$_3$—COOAlK  VI wherein Hal is chlorine, bromine or iodine and AlK is alkyl of 1 to 4 carbon atoms to obtain a compound of the formula

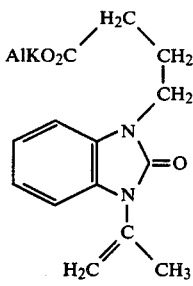  VII subjecting the latter to hydrolysis in an acid medium to obtain a compound of the formula

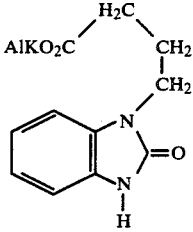  VIII subjecting the latter to saponification to obtain a compound of the formula

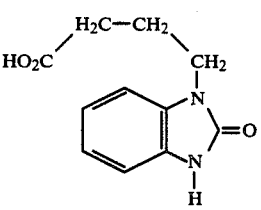  IX and cyclizing the side chain to obtain the compound of formula II.

In a preferred mode of the latter process, the alkyl halobutyrate is methyl or ethyl 4-bromobutyrate and the reaction is effected in the presence of a base such as an alkali metal hydride. The hydrolysis of compounds of formula VII is effected with an acid such as sulfuric acid in an alkanol such as methanol or ethanol and the saponification of the compounds of formula VIII is effected with a base such as sodium hydroxide or potassium hydroxide in an alkanol such as methanol or ethanol. The cyclization of compounds of formula IX is effected reacting with an agent such as thionyl chloride to obtain an acid chloride which is then treated with a Lewis acid such as aluminium chloride in an organic solvent such as methylene chloride or dichloroethane or reacting with a deshydration agent such as polyphosphoric acid.

The starting materials of formula I are known and are described in J. Chem. Soc. Perkin I, (1982), p. 261, for example.

The resolution of the racemic derivatives of formula I can be effected by classical procedures and the compounds of formula I can be converted into their acid addition salts by reacting approximately stoichiometric amounts of the acid and the free base with or without isolation.

The antihypertensive and hypotensive compositions of the invention are comprised of an antihypertensively and hypotensively effective amount of at least one compound of formula I and its non-toxic, pharmaceutically acceptable acid addition salts and an inert pharmaceutical carrier or excipient. The compositions may be in the form of tablets, dragees, gelules, granules, suppositories and injectable solutions or suspensions prepared in the usual fashion.

Examples of suitable excipients are talc, arabic gum, lactose, starch, magnesium stearate, cacao butter, aqueous and non-aqueous vehicles, fats of animal or vegetable origin, paraffinic derivatives, glycols, diverse wetting agents, dispersants and emulsifiers and preservatives.

The compositions are useful for the treatment of essential arterial hypertension, hypertension of the 50's, of menopause, of diabetics, of obesity and of plethora as well as for the treatment of arterial hypertension in the elderly or due to arteriosclerosis and for the treatment of hypertension of renal origin. They are also useful for the treatment of peripheric circulatory insufficiencies, especially for treatment of arteritis of the lower limbs as well as for cerebral circulatory insufficiencies, for treatment of senescence and cerebral arteriopathia.

Among the preferred compositions of the invention are those wherein R is hydrogen or alkyl of 1 to 5 carbon atoms and their acid addition salts. Preferred compositions are those wherein the active compound is selected from the group consisting of (6RS,trans) 6-amino-7-hydroxy-4,5,6,7-tetrahydro-imidazo[4,5,1-j-k][1]-benzazepin-2(1H)-one, (6RS, trans) 6-ethylamino-7-hydroxy-4,5,6,7-tetrahydro-imidazo[4,5,1-j-k][1]-benzazepin-2(1H)-one, (6RS, trans) 6-methylamino-7-hydroxy-4,5,6,7-tetrahydro-imidazo-[4,5,1-j-k][1]-benzazepin-2(1H)-one and (6RS,trans) 6-isopropylamino-7-hydroxy-4,5,6,7-tetrahydro-imidazo-[4,5,1,j-k][1]-benzazepin-2(1H)-one and their non-toxic, pharmaceutically acceptable acid addition salts.

The novel method of inducing hypotensive and antihypertensive activity in warm-blooded animals, including humans, comprises administering to warm-blooded animals an hypotensively and antihypertensively active amount of at least one compound of formula I and their non-toxic, pharmaceutically acceptable acid addition salts. The compounds may be administered orally, rectally or parenterally and the usual daily dose is dependent on the condition being treated, the method of administration and the specific compound. For example, it may be 0.06 to 2.5 mg/kg with the compound of example 2 when administered orally in man for treating essential arterial hypertension.

In the following examples there are described several preferred embodiments to illustrate the invention. However, it is to be understood that the invention is not intended to be limited to the specific embodiments.

EXAMPLE 1

(6RS,trans) 6-amino-7-hydroxy-4,5,6,7-tetrahydro-imidazo[4,5,1-j-k][1]-benzazepin-2(1H)-one hydrochloride

Step A: Ethyl 1,3-dihydro-2-oxo-3-benzyl-1H-benzimidazol-1-butanoate 7.6 g of sodium hydrides as a 50% suspension in oil were added over 30 minutes with stirring to a mixture of 29.6 g of 1,3-dihydro-1-benzyl-2H-benzimidazol-2-one [described in Helv., Vol. 44 (1961), p. 1278] in 296 ml of dimethylformamide and the mixture was stirred for another 30 minutes and was cooled to 5° C. 33.9 g of ethyl 4-bromobutyrate were added dropwise to the mixture over 30 minutes and the mixture was stirred at room temperature for 3 hours and was poured into 900 ml of iced water. The mixture was extracted with ether and the organic phase was washed with water, dried and evaporated to dryness. The oil residue was dissolved in 50 ml of isopropyl ether and the solution was allowed to crystallize for 16 hours and was then vacuum filtered to obtain 22.6 g of ethyl 1,3-dihydro-2-oxo-3-benzyl-1H-benzimidazol-1-butanoate melting at ≃50° C. and at 52° C. after crystallization from cyclohexane.

Analysis: $C_{20}H_{22}N_2O_3$; molecular weight=338.39. Calculated: %C 70.98, %H 6.55, %N 8.28. Found: %C 70.8, %H 6.6, %N 8.2.

Step B: 1,3-dihydro-2-oxo-3-benzyl-1H-benzimidazol-1-butanoic acid

A mixture of 40.6 g of the product of Step A and 400 ml of N methanolic sodium hydroxide was refluxed for 3 hours under an inert atmosphere and was then concentrated to one half its value and was poured into one liter of iced water. The pH was adjusted to 2 by addition of concentrated hydrochloric acid and the mixture was vacuum filtered. The product was washed and dried to obtain 35.2 g of 1,3-dihydro-2-oxo-3-benzyl-1H-benzimidazol-1-butanoic acid melting at ≃166° C. and 168° C. after crystallization from ethyl acetate.

Analysis: $C_{18}H_{18}N_2O_3$; molecular weight=310.33. Calculated: %C 69.66, %H 5.84, %N 9.02. Found: %C 69.4, %H 5.9, %N 8.9.

Step C: 5,6-dihydro-1-benzyl-imidazo[4,5,1-j-k][1]benzazepin-2,7[1H,4H]-dione 21.5 ml of thionyl chloride were added to a suspension of 21.5 g of the product of Step B in 430 ml of chloroform and the mixture was refluxed for 75 minutes and was evaporated to dryness under reduced pressure. The residue was dissolved in 860 ml of dichloroethane under an inert atmosphere and after cooling the mixture to 15° C., 18.67 g of aluminum chloride were added thereto. The mixture was stirred at 20° C. for 4 hours and was poured into one liter of iced water. 43 ml of concentrated hydrochloric acid were added thereto and the mixture was stirred for 10 minutes and was filtered. The decanted aqueous phase was extracted with methylene chloride and the combined organic phases were washed with aqueous 10% potassium carbonate to a pH of 6 and were dried and evaporated to dryness under reduced pressure. The residue was crystallized from ethyl acetate and dried to obtain 8.7 g of 5,6-dihydro-1-benzyl-imidazo[4,5,1-j-k][1]benzazepin-2,7[1H,4H]-dione melting at 135° C. after crystallization from isopropanol.

Analysis: $C_{18}H_{16}N_2O_2$; molecular weight=292.32. Calculated: %C 73.95, %H 5.51, %N 9.58. Found: %C 73.9, %H 5.5, %N 9.4.

Step D: 5,6-dihydro-imidazo[4,5,1-j-k][1]benzazepin-2,7-[1H,4H]-dione

A mixture of 29.2 g of the product of Step C, 292 g of o-phosphoric acid and 14.1 g of phenol were heated at 150° C. under an inert atmosphere for 2 hours, was cooled to about 35° C. and was poured into 1200 ml of iced water with stirring. 2 liters of methylene chloride were added to the mixture which was then made alkaline with sodium hydroxide. The mixture was filtered and the solids were washed with methylene chloride. The combined organic phases were washed, dried and evaporated to dryness under reduced pressure. The residue was crystallized and was chromatographed over silica gel. Elution with a 90-2-2 ethyl acetate-methanol-triethylamine mixture yielded 9.7 g of 5,6-dihydro-imidazo[4,5,1-j-k][1]benzazepin-2,7-[1H,4H]-dione melting at 235° C.

Analysis: $C_{11}H_{10}N_2O_2$; molecular weight=202.20. Calculated: %C 65.33; %H 4.98, %N 13.85. Found: %C 65.0; %H 4.9, %N 13.7.

Step E: 6-oxime of 4,5-dihydro-imidazo[4,5,1-j-k][1]benzazepin-2,6,7[1H]-trione 42.5 ml of 1.8N ethanolic hydrochloric acid and 10.5 ml of tert.-butyl nitrite were added at 5° C. under an inert atmosphere to a suspension of 15.5 g of the product of Step D in 620 ml of tetrahydrofuran and the mixture was stirred at 5° C. for 3 hours and was vacuum filtered. The product was washed with tetrahydrofuran and with a 1-1 chloroform-methanol mixture to obtain 16.5 g of 6-oxime of 4,5-dihydroimidazo[4,5,1-j-k][1]benzazepin-2,6,7[1H]-trione melting at >280° C.

Step F: (6RS,trans) 6-amino-7-hydroxy-4,5,6,7-tetrahydro-imidazo[4,5,1-j-k][1]benzazepin-2[1H]-one hydrochloride A suspension of 4 g of the product of Step E, 2 g of 10% palladium carbon and 150 ml of methanol was stirred under hydrogen for 2½ hours and was then filtered. The filtrate was cooled in an ice bath while slowly adding with mild stirring 0.66 g of sodium borohydride and the mixture was stirred at 5° C. for 90 minutes. The mixture was evaporated to dryness under reduced pressure at 30° C. and the residue was dissolved in 15 ml of methanol. The solution was acidified to a pH of 1-2 by addition of hydrogen chloride in ethyl acetate and the mixture was vacuum filtered to obtain 3.6 g of (6RS, trans) 6-amino-7-hydroxy-4,5,6,7-tetrahydro-imidazo[4,5,1-j-k][1]benzazepin-2[1H]-one hydrochloride melting at >260° C. before and after crystallization from methanol and then from ethanol.

Analysis: $C_{11}H_{14}N_3ClO_2$; molecular weight=255.7. Calculated: %C 51.66, %H 5.51, %N 16.43, %Cl 13.86. Found: %C 51.5, %H 5.6, %N 16.7, %Cl 14.2.

EXAMPLE 2

(6RS, trans) 6-ethylamino-7-hydroxy-4,5,6,7-tetrahydro-imidazo[4,5,1-j-k][1]benzazepin-2[1H]-one 2.18 ml of acetaldehyde and 10 ml of triethylamine were added with stirring under an inert atmosphere to a suspension of 5 g of the product of Example 1 in 200 ml of methanol and the mixture was stirred for one hour at room temperature and was cooled in an ice bath. 10 g of sodium borohydride were added over one hour and the mixture was stirred at 5° C. for one half hour and at room temperature for one hour. The methanol was evaporated and the residue was taken up in methylene chloride. The solution was washed with water and then with aqueous saturated sodium chloride solution, dried and evaporated to dryness under reduced pressure. The residue was crystallized from ethyl acetate and vacuum filtered to obtain 2.6 g of (6RS, trans) 6-ethylamino-7-hydroxy-4,5,6,7-tetrahydro-imidazo[4,5,1-j-k][1]benzazepin-2[1H]-one melting at ≃190° C.

4.2 g of the said base were dissolved in 80 ml of refluxing ethanol and the solution was cooled in an ice bath while 10 ml of ethyl acetate saturated with hydrogen chloride were added thereto. The mixture was evaporated to dryness and the residue was taken up in 30 ml of ether. The mixture was vacuum filtered and the product was crystallized from ethanol to obtain 3.14 g of the hydrochloride of the said base melting at ≃230° C.

Analysis: $C_{13}H_{18}N_3O_2Cl$; molecular weight=283.75. Calculated: %C 55.02, %H 6.39, %N 14.81, %Cl 12.49. Found: %C 55.1, %H 6.4, %N 14.4, %Cl 12.3.

EXAMPLE 3

(6RS-trans) 6-methylamino-7-hydroxy-4,5,6,7-tetrahydro-imidazo[4,5,1-j-k][1]-benzazepin-2(1H)-one hydrochloride Step A: (6RS-trans) 6-benzylamino-7-hydroxy-4,5,6,7-tetrahydro-imidazo[4,5.1-j-k][1]-benzazepin-2(1H)-one A mixture of 1 g of the compound of Example 1, 13 ml of methanol, 2 ml of triethylamine and 1 ml of benzaldehyde was stirred at room temperature under an inert atmosphere for one hour and was iced while adding 1 g of sodium borohydride over 15 minutes. The mixture was stirred for 45 minutes and 100 ml of water were then added thereto. The mixture was extracted with methylene chloride and the organic phase was washed with water, dried, filtered and evaporated to dryness under reduced pressure. The residue was chromatographed over silica gel and was eluted with a 90-5-5 ethyl acetate-methanol-triethylamine mixture. The product was crystallized from ethyl acetate to obtain 820 mg of (6RS-trans) 6-benzylamino-7-hydroxy-4,5,6,7-tetrahydro-imidazo[4,5,1-j-k][1]-benzazepin-2(1H)-one melting at ≃145° C.

Analysis: $C_{18}H_{19}N_3O_2$; molecular weight=309.36. Calculated: %C 69.88; %H 6.19, %N 13.58. Found: %C 69.6, %H 6.2, %N 13.4.

Step B: (6RS-trans) 6-(methyl-benzylamino)-7-hydroxy-4,5,6,7-tetrahydro-imidazo[4,5,1-j-k][1]benzazepin-2(1H)-one Methyl bromide was bubbled for 2 hours at room temperature through a solution of 4.6 g of the product of Step A, 11.5 ml of triethylamine and 69 ml of methanol and the mixture was evaporated to dryness under reduced pressure. The residue was taken up in 100 ml of aqueous saturated sodium bicarbonate solution and the solution was extracted with methylene chloride. The organic phase was washed with water, dried and evaporated to dryness under reduced pressure. The residue was crystallized from ethyl acetate and was vacuum filtered to obtain 4.3 g of (6RS-trans) 6-(methyl-benzylamino)-7-hydroxy-4,5,6,7-tetrahydro-imidazo[4,5,1-j-k][1H]benzazepin-2(1H)-one melting at 228° C. and at 232° C. after crystallization from ethanol.

Analysis: $C_{19}H_{21}N_3O_2$; molecular weight=323.38. Calculated: %C 70.56, %H 6.55, %N 13.00. Found: %C 70.3, %H 6.5, %N 12.8.

Step C: (6RS-trans) 6-methylamino-7-hydroxy-4,5,6,7-tetrahydro-imidazo[4,5,1-j-k][1]-benzazepin-2(1H)-one hydrochloride A mixture of 450 mg of the product of Step B, 225 mg of 10% palladized carbon and 45 ml of ethanol was stirred under hydrogen for one hour and was then filtered. The filtrate was evaporated to dryness under reduced pressure and the oil residue was dissolved in 5 ml of ethanol. The solution was filtered and excess ethyl acetate saturated with hydrogen chloride was added to the filtrate. The mixture was allowed to crystallize and was then vacuum filtered. The product was washed with ethanol and was crystallized from methanol to obtain 110 mg of (6RS-trans) 6-methylamino-7-hydroxy-4,5,6,7-tetrahydro-imidazo-[4,5,1-j-k][1]-benzazepin-2(1H)-one hydrochloride melting at 280°–290° C.

Analysis: $C_{12}H_{16}N_3O_2Cl$; molecular weight=269.93. Calculated: %C 53.43, %H 5.98, %N 15.58, %Cl 13.15. Found: %C 53.2, %H 5.9, %N 15.4, %Cl 13.4.

EXAMPLE 4

Using the procedure of Example 2, propionaldehyde was reacted and the 5.1 g of raw product was taken up in 15 ml of ethanol. 15 ml of ethyl acetate saturated with hydrogen chloride and 30 ml of ethyl acetate were added thereto and the mixture was vacuum filtered to obtain 3.8 g of (6RS-trans) 6-propylamino-7-hydroxy-4,5,6,7-tetrahydro-imidazo-[4,5,1-j-k][1]-benzazepin-2(1H)-one hydrochloride melting at ≃210° C.

EXAMPLE 5

Using the procedure of Example 2, butylaldehyde was reacted and the 2.5 g of base were taken up in 10 ml of ethanol 10 ml of ethyl acetate saturated with hydrogen chloride were added to the solution which was then vacuum filtered to obtain 1.5 g of (6RS-trans) 6-butylamino-7-hydroxy-4,5,6,7-tetrahydro-imidazo-[4,5,1-j-k][1]-benzazepin-2(1H)-one hydrochloride melting at ≃210° C.

EXAMPLE 6

Using the procedure of Example 5, pivalic aldehyde was reacted to obtain 2.2 g of (6RS-trans) 6-(2,2-dimethylpropylamino)-7-hydroxy-4,5,6,7-tetrahydro-imidazo[4,5,1-j-k][1]-benzazepin-2(1H)-one hydrochloride melting at ≃260° C.

EXAMPLE 7

(6RS-trans) 6-(2-hydroxyethylamino)-7-hydroxy-4,5,6,7-tetrahydro-imidazo[4,5,1-j-k][1]-benzazepin-2(1H)-one hydrochloride A mixture of 10.24 g of the product of Example 1, 4.8 g of glycoaldehyde, 14 ml of triethylamine and 400 ml of methanol was stirred at room temperature for one hour and was cooled to 0° to 5° C. while 10.24 g of sodium borohydride were added thereto over 15 minutes. The mixture was stirred at room temperature for 45 minutes and 100 ml of water were added thereto. The mixture was evaporated under reduced pressure to a volume of 100 ml and was allowed to crystallize at room temperature for 2 hours. The mixture was vacuum filtered to obtain 6.3 g of raw (6RS-trans) 6-(2-hydroxyethyl amino)-7-hydroxy-4,5,6,7-tetrahydro-imidazo[4,5,1-j-k][1]-benzazepin-2(1H)-one melting at 220° C.

450 mg of the said base were reacted as in Example 4 to obtain 280 mg of the hydrochloride melting at 242° C. The product was crystallized from refluxing methanol to obtain 67 mg of the hydrochloride melting at 245° C.

EXAMPLE 8

Using the procedure of Example 2, cyclohexanone was reacted to obtain 6.2 g of (6RS-trans) 6-cyclohexylamino-7-hydroxy-4,5,6,7-tetrahydro-imidazo[4,5,1-j-k][1]-benzazepin-2(1H)-one. Using the procedure of Example 4 the latter was reacted to obtain 4.2 g of the hydrochloride melting at ≃280° C. which was crystallized from methanol to obtain 3.4 g of the hydrochloride melting at 280° C.

EXAMPLE 9

Using the procedure of Step A of Example 3, (6RS-trans) 6-benzylamino-7-hydroxy-4,5,6,7-tetrahydro-imidazo-[4,5,1-j-k][1]-benzazepin-2(1H)-one melting at 145° C. was prepared and 3.5 g of the said product were dissolved in 70 ml of refluxing isopropanol. The mixture was iced and an excess of ethyl acetate saturated with hydrogen chloride was slowly added thereto. The mixture was vacuum filtered to obtain 3.85 g of the hydrochloride of the said base melting at ≃240° C. after crystallization from isopropanol.

EXAMPLE 10

Using the procedure of Example 2, phenylacetaldehyde was reacted to obtain after chromatography over silica gel and elution with a 9-1 methylene chloride-methanol (6RS,trans) 6-[2-phenethylamino]-7-hydroxy-4,5,6,7-tetrahydro-imidazo[4,5,1-j-k][1]-benzazepin-2(1H)-one and then, by the process of Example 4 its hydrochloride melting at 190° C.

EXAMPLE 11

Using the procedure of Example 2, phenoxyacetaldehyde was reacted and the product was chromatographed over silica gel. Elution with a 9-1 methylene chloride-methanol mixture and crystallization from isopropanol yielded (6RS, trans) 6-(2-phenoxyethylamino)-7-hydroxy-4,5,6,7-tetrahydro-imidazo-[4,5,1-j-k][1]-benzazepin-2(1H)-one melting at ≃150° C.

The said base was dissolved in a refluxing mixture of methylene chloride and isopropanol and the solution was concentrated. Ethyl acetate saturated with hydrogen chloride was added to the mixture which was allowed to crystallize for 2 hours at room temperature was vacuum filtered to obtain the corresponding hydrochloride melting at ≃250° C.

EXAMPLE 12

(6RS,trans) 6-(1-methyl-4-piperidinylamino)-7-hydroxy-4,5,6,7-tetrahydro-imidazo[4,5,1-j-k][1]-benzazepin-2(1H)-one dihydrochloride A mixture of 7.6 g of (6RS,trans) 6-amino-7-hydroxy-4,5,6,7-tetrahydro-imidazo[4,5,1-j-k][1]-benzazepin-2(1H)-one, 7.6 ml of N-methyl-4-piperidone, 380 ml of methanol and 7.6 g of sodium cyanoborohydride was stirred at room temperature for 24 hours and after cooling to less than 0° C., 5 ml of concentrated hydrochloric acid were added thereto dropwise. The mixture was stirred at room temperature for 10 minutes and was cooled to 0° C. and adjusted to a pH of 8 by addition of sodium hydroxide. The methanol was evaporated and the residue was taken up in methylene chloride containing 10% methanol. The mixture was filtered and the filtrate was evaporated to dryness. The residue was chromatographed over silica gel and was eluted with an 80-15-5 ethyl acetate-methanol-ammonium hydroxide mixture to obtain 7.3 g of (6RS,trans) 6-(1-methyl-4-piperidinylamino)-7-hydroxy-4,5,6,7-tetrahydro-imidazo[4,5,1-k][1]-benzazepin-2(1H)-one. The said base was dissolved in 40 ml of ethanol and 20 ml of ethanolic hydrogen chloride were added thereto. The mixture was vacuum filtered to obtain 7 g of the dihydrochloride melting at ≃260° C.

Analysis: $C_{17}H_{24}N_4O_2 \cdot 2HCl$; molecular weight=389.32. Calculated: %C 52.44, %H 6.73, %N 14.36, %Cl 18.21. Found: %C 52.5, %H 7, %N 14.3, %Cl 18.0.

EXAMPLE 13

(6RS,trans) 6-isopropylamino-7-hydroxy-4,5,6,7-tetrahydro-imidazo[4,5,1-j-k][1]-benzazepin-2(1H)-one hydrochloride 3 g of sodium cyanoborohydride were added over 15 minutes at 0° to 5° C. to a mixture of 6 g of (6RS, trans) 6-amino-7-hydroxy-4,5,6,7-tetrahydro-imidazo[4,5,1-j-k][1]-benzazepin-2(1H)-one, 60 ml of methanol and 30 ml of acetone and the mixture was stirred at room temperature for 3 hours and was evaporated to dryness under reduced pressure. The residue was added to 60 ml of water and the mixture was extracted with chloroform. The organic phase was dried and evaporated to dryness to obtain 3.6 g of (6RS,trans) 6-isopropylamino-7-hydroxy-4,5,6,7-tetrahydro-imidazo[4,5,1-j-k][1]-benzazepin-2(1H)-one melting at ≃166° C. The latter was dissolved in 60 ml of ethanol and ethyl acetate saturated with hydrogen chloride was added thereto. The mixture was vacuum filtered to obtain 3.7 g of the corresponding hydrochloride melting at ≃270° C. The product was dissolved in hot methanol and ethyl acetate was added to obtain 3.3 g of the said product melting at ≃270° C.

Analysis: $C_{14}H_{20}N_3O_2Cl$; molecular weight=297.78. Calculated: %C 56.46, %H 6.77, %N 14.11, %Cl 11.90. Found: %C 56.5, %H 6.9, %N 14.0, %Cl 12.1.

EXAMPLE 14

4,5-dihydro-imidazo[4,5,1-j-k][1]-benzazepin-2,7-(1H,6H)-dione

Step A: Ethyl 2,3-dihydro-3-(1-methyl-ethenyl)-2-oxo-1H-benzimidazol-1-butanoate A solution of 19 g of 1,3-dihydro-1-(1-methylethenyl)-2H-benzimidazol-2-one [described in J. Chem. Soc. Perkins, 1982, p. 261] in 150 ml of dimethylformamide was added with stirring at 20° C.±2° C. to 5.75 g of sodium hydride as a 50% suspension in oil and 10 ml of dimethylformamide and the mixture was stirred for another 30 minutes. 23.4 g of ethyl 4-bromo-butyrate were added to the mixture over 15 minutes and the mixture was stirred at room temperature for 4 hours and was poured into 800 ml of iced water. The mixture was extracted with ether and the organic phase was washed with water, dried and evaporated to dryness under reduced pressure to obtain 33 g of ethyl 2,3-dihydro-3-(1-methyl-ethenyl)-2-oxo-1H-benzimidazol-1-butanoate.

Step B: Ethyl 2,3-dihydro-2-oxo-1H-benzimidazol-1-butanoate 31.4 g of the product of Step A were added at 0° to 5° C. to a mixture of 15.5 ml of sulfuric acid in 155 ml of ethanol and the mixture was stirred at 0° to 5° C. for 5 hours. The mixture was neutralized with sodium hydroxide and was poured into 1.5 liters of iced water. The mixture was stirred for 5 minutes and was vacuum filtered. The product was washed with water to obtain 22 g of ethyl 2,3-dihydro-2-oxo-1H-benzimidazol-1-butanoate melting at 88° C.

Step C: 2,3-dihydro-2-oxo-1H-benzimidazol-1-butanoic acid

A solution of 22 g of the product of Step B, 22 ml of sodium hydroxide solution and 200 ml of methanol was refluxed for one hour and the methanol was evaporated. The residue was taken up in 1.5 liters of iced water and the pH was adjusted to 1 by addition of concentrated hydrochloric acid. The mixture was vacuum filtered and the product was washed with water to obtain 18.1 g of 2,3-dihydro-2-oxo-1H-benzimidazol-1-butanoic acid melting at 180° C. The product was crystallized from isopropanol to obtain 15.2 g of product melting at 185° C.

Step D: 4,5-dihydro-imidazo[4,5,1-j-k][1]-benzazepin-2,7-(1H,6H)-dione

A mixture of 15.2 g of the acid of Step C, 300 ml of chloroform and 15.2 ml of thionyl chloride was refluxed for 90 minutes and was cooled to 15° C. after which 18.4 g of aluminum chloride were added thereto all at once. The mixture was stirred for 4 hours at room temperature and was poured into 600 ml of iced water containing 15 ml of concentrated hydrochloric acid. The mixture was stirred for 5 minutes and was vacuum filtered to obtain 9.9 g of raw product and another 2.5 g of product were obtained from the mother liquor. The combined products were crystallized from isopropanol to obtain 8.5 g of 4,5-dihydro-imidazo-[4,5,1-j-k][1]-benzazepin-2,7-(1H,6H)-dione melting at 238° C.

EXAMPLE 15

Tablets were prepared containing either 10 mg of (6RS,trans) 6-methylamino-7-hydroxy-4,5,6,7-tetrahydro-imidazo-[4,5,1-j-k][1]benzazepin-2-(1H)-one hydrochloride or of (6RS, trans) 6-isopropylamino-7-hydroxy-4,5,6,7-tetrahydro-imidazo[4,5,1-j-k][1]-benzazepin-2(1H)-one hydrochloride or 20 mg of (6RS,trans) 6-ethylamino-7-hydroxy-4,5,6,7-tetrahydro-imidazo-[4,5,1-j-k][1]-benzazepin-2(1H)-one hydrochloride and sufficient excipient of lactose, starch, talc and magnesium stearate for a final tablet of 100 mg.

PHARMACOLOGICAL DATA

A. Hypotensive Activity

The hypotensive activity was determined on male rats of the Wistar strain weighing about 300 g and anesthesized with 50 mg/kg intraveinously of sodium pentobarbital. The test product was intraveinously administered into the penile vein or the jugular vein and the carotidien arterial pressure was measured before and after the administration of the test compound and the variations expressed as a percentage of arterial pressure after administration of the test product as compared to the initial control arterial pressure is reported in Table I.

TABLE I

| Products of Example | Dose in mg/kg | % Variation of arterial pressure minutes after administration | | | |
|---|---|---|---|---|---|
| | | 1 minute | 5 minutes | 10 minutes | 30 minutes |
| 1 | 10 | −54 | −46 | −43 | −30 |
| | 1,0 | −25 | −11 | −11 | −9 |
| 2 | 10 | −59 | −53 | −54 | −51 |
| | 1,0 | −34 | −23 | −19 | −18 |
| | 0,1 | −18 | −7 | −9 | −7 |
| 3 | 1,0 | −33 | −21 | −22 | −17 |
| 4 | 1,0 | −42 | −23 | −9 | −5 |
| 5 | 1,0 | −36 | −16 | −9 | −4 |
| 6 | 10 | −44 | −32 | −32 | −23 |
| | 1,0 | −21 | −7 | −4 | +5 |
| 7 | 10 | −53 | −29 | −29 | −19 |
| 10 | 1,0 | −57 | −41 | −24 | −19 |
| 11 | 1,0 | −52 | −48 | −49 | −48 |
| 12 | 1,0 | −14 | −16 | −20 | −20 |
| 14 | 1,0 | −45 | −34 | −30 | −22 |
| | 0,1 | −26 | −17 | −4 | −5 |

B. Peripheric vasodilatatory Activity

The variation of pressure in an isolated vascular circuit perfused at a constant flow as a direct measurement of vasomotricity was effected on Beagle dogs of both sexes weighing between 10 to 16 kg anesthesized with an intraveinous administration of 35 mg/kg of sodium pentobarbital. A perfusion of 4.5 mg/4.5 ml/kg per hour of nembutal was effected by the saphene vein during the duration of the test. The dogs had intubation with a tracheal canule and were ventilated. After intraveinous administration of 5000 IU of heparin, the right femoral artery was catheterized and the blood which flowed after passage through an extra corporeal circuit as short as possible and reintroduced into the left femoral artery, agreeing with perfusion of the left rear paw. Above the extra-corporeal circuit is placed a constant flow pump below and in connection to a pressure collector permitting the registration of the perfusion pressure in the paw.

The arterial pressure was determined in the carotide with another pressure collector and the perfusion flow in the paw was adjusted to equalize the carotidien and femoral pressures. The left rear paw was placed in a sac containing crushed ice which led to an increase of the perfusion and the sensitivity of the paw was tested by administration of naftidrofuryl at 100, 300, 1000 and 3000 μg in a volume of 0.2 ml of distilled water. The test product was injected into the extra corporeal circuit upstream of the pump in varying doses. After the administration of the range of doses of the product, a new range of doses of naftidrofuryl was injected to permit verification of the stability of the preparation.

The lessening of the pressure shows a lessening of the muscular tone of the perfusion zone due to peripheric resistance and the effects are expressed in percentage variation in perfusion pressure in the rear paw. The compounds of Examples 3 and 14 are, respectively, 40 to 50 and 300 times more active than naftidrofuryl.

C. Acute toxicity

The $DL_0$ dose or the maximum dose which did not provoke any deaths in mice after 8 days by oral administration was determined and the results are reported in Table II.

TABLE II

| Product of Example | $DL_0$ in mg/kg |
|---|---|
| 1 | >400 |
| 2 | >400 |
| 3 | 200 |
| 4 | 200 |
| 5 | 20 |
| 6 | 60 |
| 7 | >400 |
| 10 | 20 |
| 11 | 80 |
| 12 | 100 |
| 13 | >400 |
| 14 | 200 |

Various modifications of the products and methods of the invention may be made without departing from the spirit or scope thereof and it is to be understood that the invention is intended to be limited only as defined in the appended claims.

What we claim is:

1. A compound selected from the group consisting of 6-amino-7-hydroxy-4,5,6,7-tetrahydro-imidazo[4,5,1-j-k][1]-benzazepin-2-(1H)-one derivatives of the formula

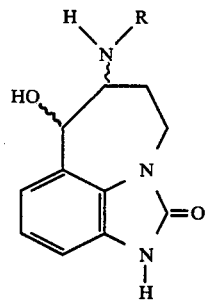

wherein R is selected from the group consisting of hydrogen, alkyl and hydroxyalkyl of 1 to 8 carbon atoms, alkyl of 1 to 8 carbon atoms substituted by phenyl or phenoxy, cycloalkyl of 3 to 7 carbon atoms, 4-piperidyl optionally substituted in the 1-position with alkyl of 1 to 4 carbon atoms and the wavy lines indicate that the 7-OH and 6-amino have the trans configuration and their non-toxic, pharmaceutically acceptable acid addition salts.

2. A compound of claim 1 wherein R is hydrogen or alkyl of 1 to 5 carbon atoms.

3. A compound of claim 1 selected from the group consisting of (6RS,trans) 6-amino-7-hydroxy-4,5,6,7-tetrahydro-imidazo-[4,5,1-j-k][1]-benzazepin-2(1H)-one and its non-toxic, pharmaceutically acceptable acid addition salts.

4. A compound of claim 1 selected from the group consisting of (6RS,trans) 6-ethylamino-7-hydroxy-4,5,6,7-tetrahydro-imidazo-[4,5,1-j-k][1]-benzazepin-2(1H)-one and its non-toxic, pharmaceutically acceptable acid addition salts.

5. A compound of claim 1 selected from the group consisting of (6RS,trans) 6-methylamino-7-hydroxy-4,5,6,7-tetrahydro-imidazo-[4,5,1-j-k][1]-benzazepin-2(1H)-one and its non-toxic, pharmaceutically acceptable acid addition salts.

6. A compound of claim 1 selected from the group consisting of (6RS,trans) 6-isopropylamino-7-hydroxy-4,5,6,7-tetrahydro-imidazo-[4,5,1-j-k][1]-benzazepin-2(1H)-one and its non-toxic, pharmaceutically acceptable acid addition salts.

7. An antihypertensive and hypotensive composition comprising an antihypertensively and hypotensively effective amount of at least one compound of claim 1 and an inert pharmaceutical excipient.

8. A composition of claim 7 wherein R is hydrogen or alkyl of 1 to 5 carbon atoms.

9. A composition of claim 7 wherein the active compound is selected from the group consisting of (6RS,trans) 6-amino-7-hydroxy-4,5,6,7-tetrahydro-imidazo-[4,5,1-j-k][1]-benzazepin-2(1H)-one and its non-toxic, pharmaceutically acceptable acid addition salts.

10. A composition of claim 7 wherein the active compound is selected from the group consisting of (6RS,trans) 6-ethylamino-7-hydroxy-4,5,6,7-tetrahydro-imidazo-[4,5,1-j-k][1]-benzazepin-2(1H)-one and its non-toxic, pharmaceutically acceptable acid addition salts.

11. A composition of claim 7 wherein the active compound is selected from the group consisting of (6RS,trans) 6-methylamino-7-hydroxy-4,5,6,7-tetrahydro-imidazo-[4,5,1-j-k][1]-benzazepin-2(1H)-one and its non-toxic, pharmaceutically acceptable acid addition salts.

12. A composition of claim 7 wherein the active compound is selected from the group consisting of (6RS,trans) 6-isopropylamino-7-hydroxy-4,5,6,7-tetrahydro-imidazo-[4,5,1-j-k][1]-benzazepin-2(1H)-one and its non-toxic, pharmaceutically acceptable acid addition salts.

13. A method of inducing antihypertensive and hypotensive activity in warm-blooded animals comprising administering to warm-blooded animals an antihypertensively and hypotensively effective amount of at least one compound of claim 1.

14. A method of claim 13 wherein R is hydrogen or alkyl of 1 to 5 carbon atoms.

15. A method of claim 13 wherein the active compound is selected from the group consisting of (6RS,trans) 6-amino-7-hydroxy-4,5,6,7-tetrahydro-imidazo-[4,5,1-j-k][1]-benzazepin-2(1H)-one and its non-toxic, pharmaceutically acceptable acid addition salts.

16. A method of claim 13 wherein the active compound is selected from the group consisting of (6RS, trans) 6-ethylamino-7-hydroxy-4,5,6,7-tetrahydro-imidazo-[4,5,1-j-k][1]-benzazepin-2(1H)-one and its non-toxic, pharmaceutically acceptable acid addition salts.

17. A method of claim 13 wherein the active compound is selected from the group consisting of (6RS, trans) 6-methylamino-7-hydroxy-4,5,6,7-tetrahydro-imidazo-[4,5,1-j-k][1]-benzazepin-2(1H)-one and its non-toxic, pharmaceutically acceptable acid addition salts.

18. A method of claim 13 wherein the active compound is selected from the group consisting of (6RS,trans) 6-isopropylamino-7-hydroxy-4,5,6,7-tetrahydro-imidazo-[4,5,1-j-k][1]-benzazepin-2(1H)-one and its non-toxic, pharmaceutically acceptable acid addition salts.

* * * * *